(12) United States Patent
Gösswein et al.

(10) Patent No.: US 7,331,698 B2
(45) Date of Patent: Feb. 19, 2008

(54) ILLUMINATION DEVICE AND MEDICAL IMAGING AND EXAMINATION DEVICE HAVING AN ILLUMINATION DEVICE

(75) Inventors: Wolfgang Gösswein, Effeltrich (DE); Ludwig Kreischer, Dormitz (DE); Markus Petsch, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 209 days.

(21) Appl. No.: 11/127,342

(22) Filed: May 12, 2005

(65) Prior Publication Data

US 2005/0254256 A1    Nov. 17, 2005

(30) Foreign Application Priority Data

May 14, 2004   (DE)   ................ 10 2004 024 095

(51) Int. Cl.
*A61B 1/06*   (2006.01)
(52) U.S. Cl. .............. 362/572; 362/33; 362/804; 333/12; 333/181
(58) Field of Classification Search ................ 362/572, 362/33, 804; 333/12, 181
See application file for complete search history.

(56) References Cited

U.S. PATENT DOCUMENTS

| 4,922,204 | A |  | 5/1990 | Duerr et al. |
| 5,355,885 | A |  | 10/1994 | Tsuda et al. |
| 5,477,858 | A | * | 12/1995 | Norris et al. ............... 600/441 |
| 6,101,038 | A | * | 8/2000 | Hebert et al. ............... 359/618 |
| 6,219,570 | B1 |  | 4/2001 | Mueller et al. |
| 6,831,551 | B2 | * | 12/2004 | Davenport et al. ......... 370/447 |
| 7,236,818 | B2 | * | 6/2007 | McLeod et al. ............ 600/509 |

FOREIGN PATENT DOCUMENTS

| DE | 38 11 983 A1 | 10/1989 |
| DE | 197 49 903 A1 | 5/1999 |

* cited by examiner

*Primary Examiner*—Sandra O'Shea
*Assistant Examiner*—Jessica L McMillan

(57) ABSTRACT

An illumination device (1,10,20,41) for illuminating an examination room (33) of an imaging medical examination device (31) has illuminants (7,21,55), which emit light when energized and can be electrically connected to a power source via connecting means (5A,5B,15A, . . . 15D), at least two of the illuminants (7,21,55) being connected by means of an electrical supply line (8) and the electrical supply line (8) having at least one high frequency filter (9,11) for reducing the interaction of the supply line (8) with a high frequency field.

17 Claims, 3 Drawing Sheets

ILLUMINATION DEVICE AND MEDICAL IMAGING AND EXAMINATION DEVICE HAVING AN ILLUMINATION DEVICE

CROSS REFERENCE TO RELATED APPLICATIONS

This application claims priority to the German application No. 10 2004 024 095.7, filed May 14, 2004 which is incorporated by reference herein in its entirety.

FIELD OF INVENTION

The invention relates to an illumination device for illuminating an examination room of an imaging medical examination device using illuminants which emit light when energized and can be electrically connected to a power source by means of connecting means. The invention refers to an imaging medical examination device with an examination room for introducing a patient, the examination room being at least partially surrounded by a boundary wall, it being possible to illuminate said examination room with at least one illumination device of this type.

BACKGROUND OF INVENTION

To increase patient comfort in imaging medical examination devices, the examination room of the device is typically illuminated. In magnetic resonance devices for example, the magnet hole, which is designed cylindrically for example and comprises the imaging examination room, is illuminated. In this way, the illumination is not able to dazzle a patient located in the examination room and is to be adapted to the patient's individual requirements. Furthermore in order to cool the patient, air is blown into the examination room mostly from the opening at the rear.

SUMMARY OF INVENTION

In magnetic resonance devices, an illumination of the magnet hole mainly occurs from the outside by means of electrically powered lamps, such as halogen lamps or LED arrays. These lamps indirectly illuminate the magnet hole, in other words they radiate onto a wall bordering the examination room from the outside. For this purpose, they are assembled for example onto the rear funnel entry outside the magnet hole. Point light sources of this type are disadvantageous in that the patient is slightly dazzled. Furthermore, lamps radiating from outside the examination room are disadvantageous in that they restrict accessibility to the patient. In addition, the marked sensitivity of halogen lamps to magnetic fields present in magnetic resonance devices must potentially be accounted for, said magnetic fields deflecting a spiral through which current flows for example. This results in technically time-consuming correction measures.

In addition to the radiating lamps, it is also possible to effect the illumination directly in the patient openings using magnetic resonance tomography, computer tomography devices or radiation therapy devices. In electrically operated lamps, heavily induced high frequency currents occur in strong high frequency fields for example of magnetic resonance devices in the feed lines. As these currents are associated with strong magnetic fields, they can impermissibly increase the local SAR loading (SAR: specific absorption rate) of a patient to be examined. Therefore, purely optical solutions for lighting circuits and radiation in the examination room are known in particular in magnetic resonance devices. The illumination occurs for example via a mesh made from light conductors radiating laterally, arranged in the 12 o'clock position across the entire length of the magnet. The coupling of the light generally takes place by means of laborious and expensive lamps or projectors, which can only be designed as compatible with magnetic resonance by means of a high outlay. Disadvantageously high costs thus result not only with the light generation, but also with the light distribution due to high transport losses.

The ventilation in MR devices for example is typically effected by an air current generated through a ventilator, which is directed through tubes to one or more nozzles, which guide the air at the rear funnel into the examination room. To ensure a cooling flow of air in the magnet hole, the air is blown into the upper region and flows in many known solutions from back to front across the body of the patient. With an unfavorable position of the patient in the examination room, this can be felt to be an unpleasant blast of air in the patient's face.

A cladding wave trap with an inductivity designed using a toroid shape is known from DE 38 11 983 A1, as can be used for example in a high frequency antenna of an MR device.

One object of the invention is to specify an illumination device which enables a simple, in particular magnetic-field-compatible illumination of the examination room. A further object is to specify an imaging medical examination device of this type.

The object mentioned at first in relation to the illumination device mentioned at the start is achieved in that at least two of the illuminants are connected by means of an electrical supply line, the electrical supply line comprising at least one high frequency filter to reduce the interaction of the supply line with a high frequency field. The invention is advantageous in that the high frequency currents can be heavily reduced by means of high frequency filters.

These objects are achieved by the claims. The invention is advantageous in that the high frequency currents can be heavily reduced by means of high frequency filters. High frequency fields are for example magnetic high frequency fields in the case of magnetic resonance devices. Magnetic-field-compatible illumination devices are directly important in relation to high field magnetic resonance tomography devices since currents resulting in these devices during illumination can result in an increased local SAR loading of the patient.

As a result of the magnetic-field-compatible design of the illumination device, the examination device is advantageous in that the illumination device, in magnetic resonance devices for example, can also be arranged in regions with strong high frequency fields. This type of illumination device essentially does not restrict accessibility to the patient. A further advantage exists in that costly magnetic-resonance-compatible high performance illuminant sources for light generation and for coupling in a fiber bundle as well as the expensive light-conducting system made from optical fibers required therefore are dispensed with.

In an advantageous embodiment of the illumination device, several illuminants are electrically connected with one another as a series connection, the series connection comprising consecutive illuminants and high frequency filters which are electrically connected to one another by means of supply lines.

This is advantageous in that large-area distributed arrangements of illuminants are possible with the aid of the series connection. The illuminants are preferably distributed in a laminar and dazzle-free manner. This is advantageous in that an agreeable illumination is possible. By way of example, the illuminants and/or the entire series connection is configured as a printed circuit board, preferably in units configured modularly. The latter simplifies an exchange of defective illuminants for instance.

In an advantageous embodiment a first illuminant connected in series is electrically connected to its associated connecting means and/or a final illuminant connected in series is electrically connected with its associated connecting means via at least one further high frequency filter in each instance. In this case, the feed lines to the first and/or the last illuminant are also designed to be compatible with the magnetic field.

Examples of high frequency filters are non-magnetic air-core chokes or cladding wave traps, such as those known from DE 38 11 983 A1.

Examples of illuminants designed to be magnetic-field-compatible are light-emitting diodes or multicolor light-emitting diodes. The latter are advantageous in that their color emission can be individually adjusted by connection with several power sources. In the case of multicolor light-emitting diodes, it is advantageous that the electrical supply lines have several electrical conductors to link different connections. With a corresponding design of the high frequency filters, a cladding wave trap for example, the lines can be decoupled together from the magnetic field via a high frequency filter.

In an advantageous embodiment, the series connection restricted by the connecting means is divisible into an outgoing section and a return section, the sections being essentially the same length and the direction of flow being opposite to an essentially identical current during operation of the illumination device in order to avoid a magnetic field generated by the current flow. With this embodiment possible interference magnetic fields which are generated by the current flow in the outward section and return section are compensated for. It is especially advantageous to twist the outward section and return section with one another.

In an advantageous embodiment of the medical examination device, the illumination device is integrated into a housing fixed to the boundary wall. This is advantageous in that the illumination device is protected against damage.

In an advantageous development, the housing is configured so that it can be connected to an air supply device and the housing has air outlet openings for ventilating the examination room. This is advantageous in that the housing can be used for two purposes, on the one hand for ventilation and on the other hand for accommodating the ventilation device.

In an advantageous embodiment the housing is arranged between a suspension device located in the examination room for suspending the patient and the boundary wall. By way of example, said housing can be arranged on several azimuthally distributed positions on a cylinder-shaped boundary wall, as is the case with a conventional magnetic resonance device.

In a particularly advantageous development, the housing is arranged laterally next to the suspension device in order to expand a bearing area of the suspension device. Even with magnetic resonance devices with a large examination room diameter, the space next to the patient support can be used both to ventilate and also illuminate in this manner. In this way, the housing can additionally also be used as a bearing widener.

In an alternative embodiment of the illumination device, said device only has one illuminant or one illuminant unit with a plurality of illuminants, the illuminant or the illuminant unit being connected to an energy source outside the examination room by means of an electrical supply line, the electrical supply line having at least on high frequency filter for reducing the interaction of the supply line with a high frequency field. This embodiment can be designed in a similar manner to the developments described above.

Further advantageous embodiments of the invention are characterized by the features of the dependent claims.

BRIEF DESCRIPTION OF THE DRAWINGS

Several exemplary embodiments of the invention are described below with reference to the FIGS. 1 to 6, in which.

DETAILED DESCRIPTION OF INVENTION

Figure 1:
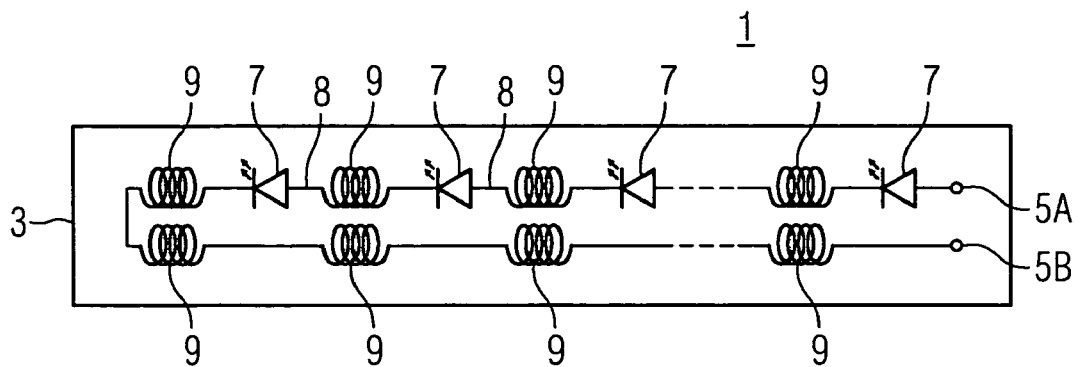
FIG. 1 shows a schematic representation of a series connection of several light-emitting diodes with an outward and a return wire.

FIG. 1 shows an exemplary design of an illumination device 1 according to the invention, which is configured as a printed circuit board 3. Based on connections 5A, 5B for connection with a direct current source (not shown) a series connection of several light-emitting diodes 7 and non-magnetic air-core chokes 9 can be recognized. In this way, two light-emitting diodes are connected in each instance via one of the air-core chokes 9 by means of a supply line 8. In the embodiment according to FIG. 1, it can be seen that light-emitting diodes are only arranged in one outward section of the series circuit, whereby an air-core choke is interconnected between two light-emitting diodes in each instance with the aid of supply lines. The same number of air-core chokes are located in a return section so that both outward and return sections can be decoupled by an interaction using magnetic high frequency fields, since a high frequency current induced by the high frequency field is suppressed. The air-core chokes function as high frequency filters and thus suppress currents on the basis of the interaction of the series connection with the magnetic high frequency field. The symmetrical design of the outward section and the return section additionally causes a static magnetic field outgoing from the supply lines to be minimized, for example in that the same current flows in the outward and return sections. With the cost-effective realization, a particularly advantageous twisting of the supply lines can be achieved as a printed circuit board by a cyclical exchange of positions of circuit paths.

Figure 2:
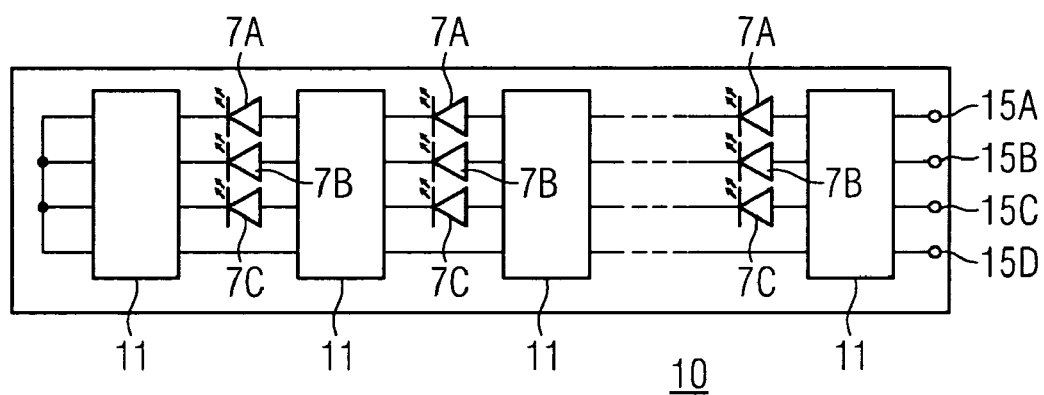
FIG. 2 shows an illumination device, in which the three series connections are connected in parallel in the outward wire, and the outward and return wires are each high-frequency-decoupled with cladding wave traps.

FIG. 2 shows an illumination device 10 differing in two aspects from the design in FIG. 1. On the one hand, the chokes in the supply lines are replaced by common cladding wave traps 11 which now suppress the induced high frequency current.

Furthermore, the design differs in that three outward sections guided in each instance in parallel are used for illumination. If different colored light-emitting diodes 7A, 7B, 7C are used in them, individual colors and saturation levels can be generated by additive color mixing. This is advantageous compared with the subtractive methods used for example in purely optical light transmission systems by means of color filters. The color output can be controlled individually via several direct current sources connected to the connections 15A, . . . 15D, by a medical technical assistant for example. The control possibilities additionally allow a transmission of important simple patient information by means of a remote-controlled presentation of the light situation, for example by preparing for a measurement in a well illuminated examination room and the issue of a command to hold the breath by means of a color change etc.

Figure 3:
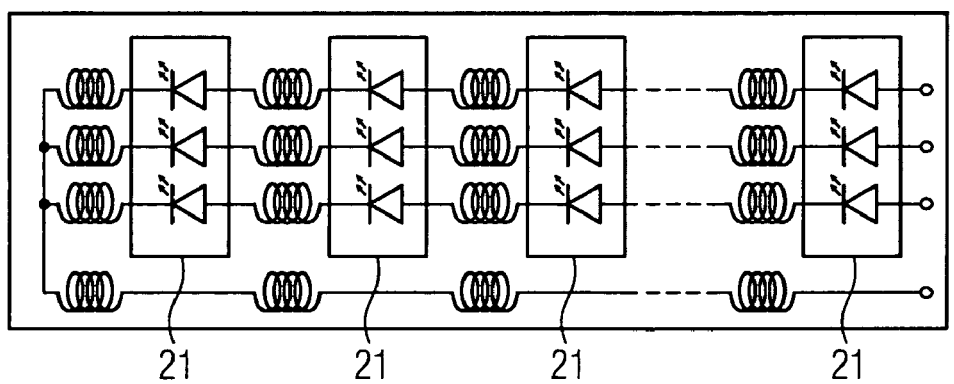
FIG. 3 shows a similar circuit diagram to FIG. 2 with multicolor light-emitting diodes.

FIG. 3 shows a further exemplary illumination device 20 with so-called multicolor light-emitting diodes 21 (RGB_LEDs), in which the individually controlled primary colors red, yellow, blue can be generated in a common light-emitting diode unit.

Figure 4:
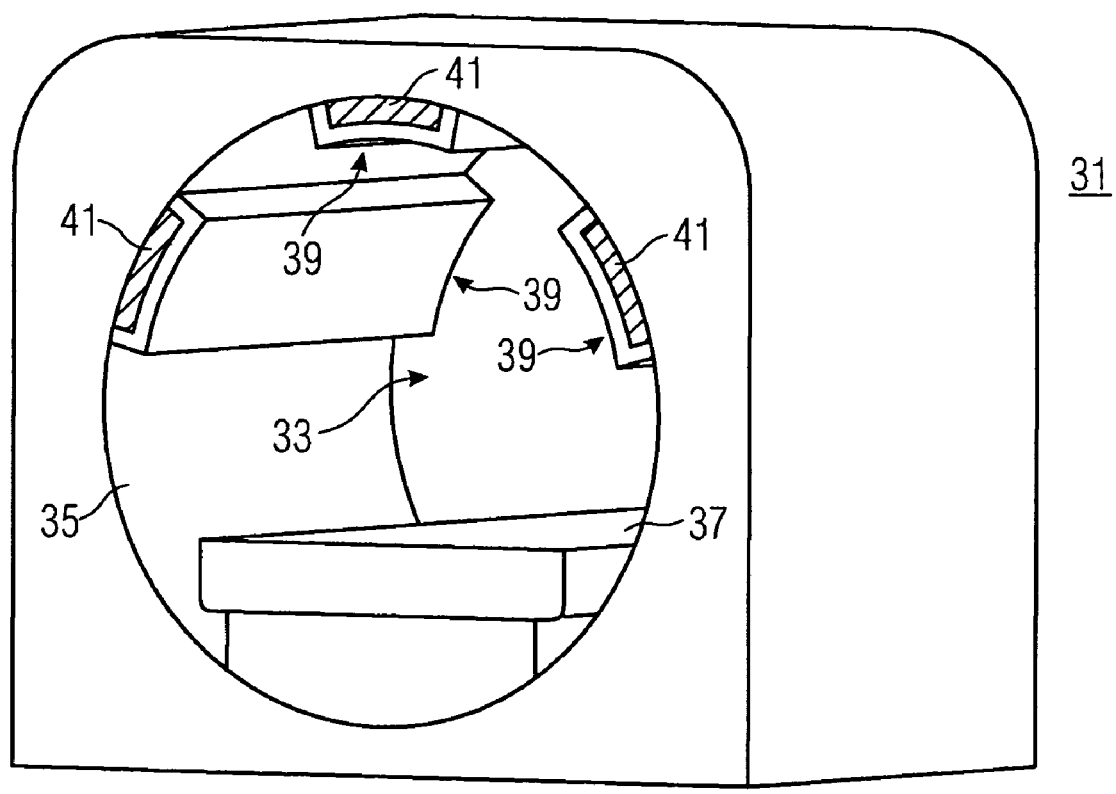
FIG. 4 shows a possible arrangement of three illumination devices, which are arranged azimuthally on a cylinder shaped boundary wall surrounding the examination room.

FIG. 4 shows an imaging medical examination device 31, for example a magnetic resonance device or computer tomography device comprising an examination room 33 which is at least partially surrounded by a boundary wall 35. The boundary wall is for example the innermost housing wall of a hollow cylinder-shaped whole body high frequency antenna system. A patient can be brought into the examination room 33 for example with the aid of a patient support 37. The illumination of the examination room 33 takes place with printed circuit board illumination devices 41 protected by the housing 39, said illumination devices being arranged concentrically above and left and right on the cylinder-cladding-shaped boundary wall 35. The housing 39 can be fixed for example to the boundary wall 35 by means of clip-on mechanisms or can be screwed or glued.

Figure 5:
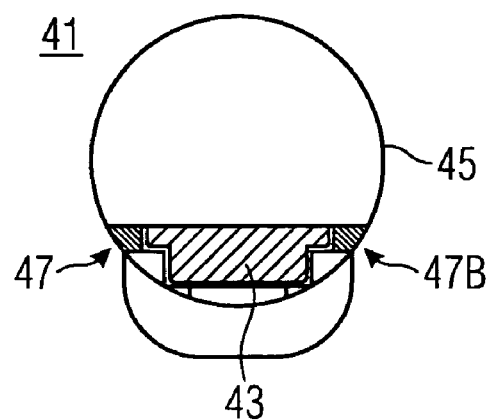
FIG. 5 shows a possible arrangement of two oblong illumination devices with housing, which lie parallel to a patient support in the examination room

A particularly advantageous arrangement of the illumination devices is possible in novel magnetic resonance systems with large patient holes. FIG. 5 shows a cross-section through a magnetic resonance device 41 of this type with a boundary wall 45, displaying a lining of the examination device. Based on the size of the diameter, the patient support 43 no longer takes up the entire region from the boundary wall 45 on the one side to the boundary wall 45 on the other side. In this way, two free spaces 47A, 47B result on both sides of the patient support 43, which can be used to illuminate and to ventilate the examination room. To this purpose, an illumination device extends next to the patient support across the entire length of the hollow cylindrically shaped magnetic resonance device. It thus does not cause interference even in the case of access to the examination room or to the patient. A bordering cover surface of the elongated housing of the illumination device additionally allows the support surface of the patient support 43 to be widened and air to be blown in at several locations. An exemplary design of this is shown in FIG. 6.

Figure 6:
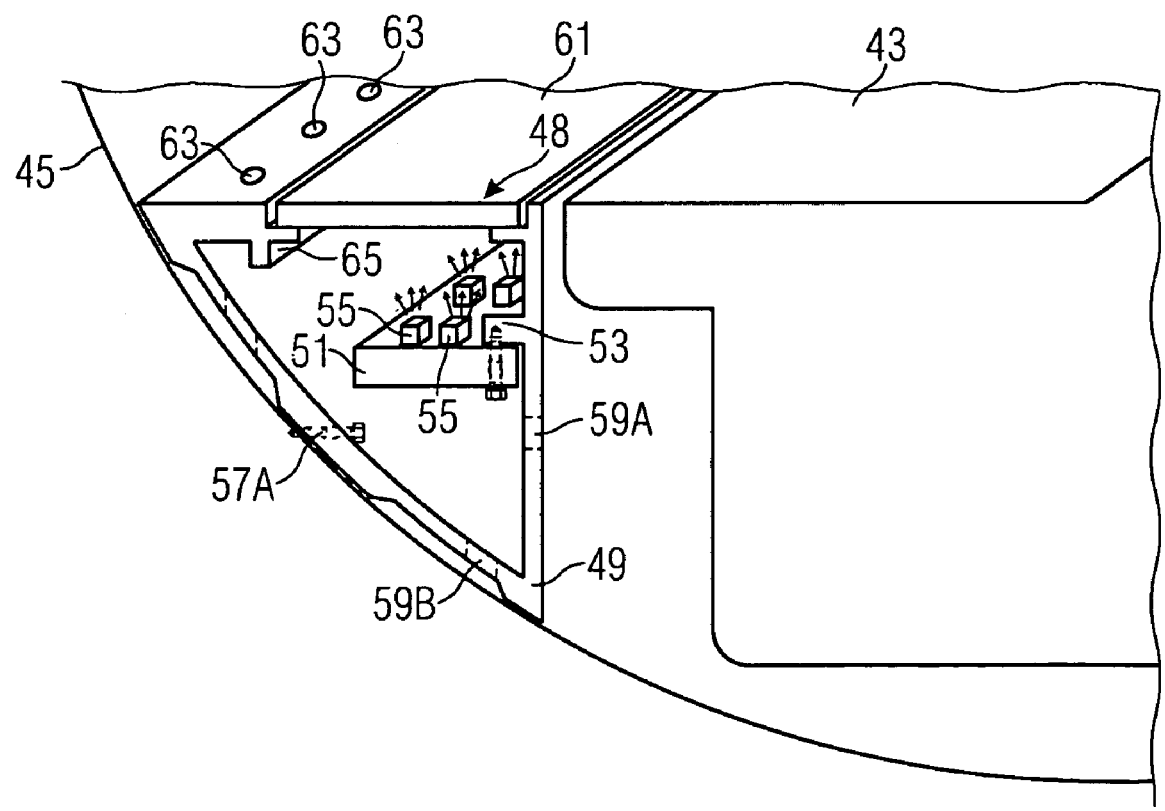
FIG. 6 shows a cross-section through a left-hand illumination device from FIG. 5.

FIG. 6 shows the patient support 43 in a section through the MR device from FIG. 5, the surface of which merges flush into a covering surface 48 except for a gap. It may be favorable to adjust an angle between the covering surface 48 and the top of the patient support so as to effect certain illumination and/or ventilation effects. The covering surface 48 is the top side of a housing 49, that is arranged parallel to the patient support 43 in an elongated gap between the patient support 43 and the boundary wall 45, and is integrated into the at least one illumination device. By way of example, a circuit board 51 with an illumination device according to FIGS. 1 to 3 within the housing is screwed onto a projection 53, whereby LEDs 55 forming a series connection radiate single-colored light or multicolor light upwards.

The housing 49 itself is screwed onto the boundary wall 45 by means of a screw 57. The housing wall has recesses 59A, 59B for inserting a screwdriver and for introducing the screws. The upper side of the housing has a diffuser plate 61, which radiates the emitted light of the light-emitting diodes 55A, so that a dazzle-free effect results for a patient or operating operative. The diffuser plate is also screwed on for instance. The hollow space of the elongated housing 49 can additionally be used for ventilation. To this purpose, ventilation holes 63 are arranged in the covering surface 47. In order to prevent light scattering at these holes, the housing is provided with a shading ridge 65.

An electrical supply of the illumination device is located on the end plates connected lengthwise, via connections to a direct current source integrated into the MR device current supply. Furthermore, air is blown into the housing at the end plates with a slight overpressure and then flows into the examination room through outlet openings 63. In this way, inflowing air has the particular advantage that the patient in the examination device no longer feels an irritating draft on his/her face.

The illumination device is electrically connected to one or in the case of multicolor light-emitting diodes to several direct current voltage supplies. Accordingly, the illumination can be dimmed by means of the current and/or adjusted in its coloring.

Illumination devices of this type can be attached to a pole disk for instance, even in the case of open magnet resonance devices with two opposite disk-shaped pole disks generating the basic magnetic field.

The invention claimed is:

1. An illumination device for illuminating an examination space of a medical imaging and examination device, comprising:
   a plurality of illuminants configured to emit light when energized and to be electrically connected to a power source using a connecting device;
   an electrical supply line that connects at least two of the illuminants; and
   a high frequency filter that is arranged in the electrical supply line comprising a high frequency filter, the high frequency filter configured to reduce an electromagnetic influence of the supply line on a high frequency field generated by the medical imaging and examination device,
   wherein the illuminants are connected in series, the series connection including the high frequency filter arranged between each two serially connected illuminants.

2. The illumination device according to claim 1, wherein the illuminants are distributed on a plain surface.

3. The illumination device according to claim 2, wherein a printed circuit board includes the plain surface.

4. The illumination device according to claim 1, wherein the first or last illuminant of the series connection is electrically connected to the connecting device using a further high frequency filter.

5. The illumination device according to claim 1, wherein the high frequency filter is a non-magnetic air-core choke.

6. The illumination device according to claim 1, wherein the further high frequency filter is a non-magnetic air-core choke.

7. The illumination device according to claim 1, wherein the high frequency filters is a cladding wave trap.

8. The illumination device according to claim 1, wherein the further high frequency filters is a cladding wave trap.

9. The illumination device according to claim 1, wherein at least one of the illuminants comprises at least one light-emitting diode.

10. The illumination device according to claim 9, wherein the light-emitting diode is a multicolor light-emitting diode.

11. The illumination device according to claim 10, wherein the multicolor light-emitting diode is configured to emit different colors of light based on a connection of the multicolor light-emitting diode to different power sources.

12. The illumination device according to claim 1, wherein the series connection is limited by the connecting device and includes an outward and a return section having essentially the same length and each carrying an electrical current of the same amperage but opposite flow direction for avoiding a magnetic field generated by the electrical current.

13. The illumination device according to claim 12, wherein the outward and return sections are twisted.

14. A medical imaging and examination device, comprising:
    an examination space for accommodating a patient, the examination space at least partially surrounded by a boundary wall;
    at least one illumination device arranged between the boundary wall and the examination space for illuminating the examination space, the illumination device comprising a plurality of illuminants configured to emit light when energized and to be electrically connected to a power source using a connecting device, wherein at least two of the illuminants are connected by an electrical supply line, the electrical supply line comprising a high frequency filter, the high frequency filter configured to reduce a high frequency current of the supply line induced by a high frequency field generated by the medical imaging and examination device; and
    a housing including the illumination device, the housing attached to the boundary wall,
    wherein the housing has an air outlet opening and is configured to be connected to an air supply device for ventilating the examination space.

15. The medical imaging and examination device according to claim 14, wherein the housing is arranged between a support device for accommodating a patient and the boundary wall, the support device located in the examination space.

16. The medical imaging and examination device according to claim 15, wherein a lying area of the support device includes a surface of the housing, the housing laterally attached to the support device.

17. The illumination device according to claim 10, wherein a color output of the multicolor light-emitting diode is controlled to transmit patient information.

* * * * *